United States Patent
Buechi

(10) Patent No.: US 10,118,010 B2
(45) Date of Patent: Nov. 6, 2018

(54) TEMPERATURE MEASURING DEVICE FOR A RESPIRATORY HUMIDIFIER

(71) Applicant: Hamilton Medical AG, Bonaduz (CH)

(72) Inventor: Rudolf Buechi, Chur (CH)

(73) Assignee: Hamilton Medical AG (CH)

( * ) Notice: Subject to any disclaimer, the term of this patent is extended or adjusted under 35 U.S.C. 154(b) by 487 days.

(21) Appl. No.: 14/348,964

(22) PCT Filed: Sep. 27, 2012

(86) PCT No.: PCT/EP2012/069117
§ 371 (c)(1),
(2) Date: Apr. 1, 2014

(87) PCT Pub. No.: WO2013/045569
PCT Pub. Date: Apr. 4, 2013

(65) Prior Publication Data
US 2014/0238394 A1    Aug. 28, 2014

(30) Foreign Application Priority Data
Oct. 1, 2011  (DE) .................... 10 2011 054 132

(51) Int. Cl.
*A61M 16/16* (2006.01)
*G01J 5/00* (2006.01)
(Continued)

(52) U.S. Cl.
CPC .......... *A61M 16/16* (2013.01); *A61M 16/109* (2014.02); *G01J 5/0014* (2013.01);
(Continued)

(58) Field of Classification Search
CPC .......... A61M 16/16; A61M 2205/3306; A61M 2205/3313; A61M 2205/3368;
(Continued)

(56) References Cited

U.S. PATENT DOCUMENTS 5,581,015 A    12/1996  Kiesow
5,729,653 A    3/1998   Magliochetti et al.
(Continued)

FOREIGN PATENT DOCUMENTS

DE    102007037955 A1    2/2009

*Primary Examiner* — Gregory Anderson
*Assistant Examiner* — Elliot S Ruddie
(74) *Attorney, Agent, or Firm* — Jansson Munger; McKinley & Kirby Ltd.

(57) ABSTRACT

A temperature-measuring device for a respiratory humidifier (1) with a liquid container (5) is provided, wherein the temperature-measuring device comprises a flow channel (9) for breathing gas and an infrared detector (21), which is directed from the outside toward the flow channel (9) for the contactless detection of the temperature of the breathing gas in the flow channel (9), wherein the flow channel (9) comprises on its lateral surface (13) a measurement portion (15), which is aligned with the surrounding areas of the lateral surface (13) and toward which the infrared detector (21) is directed, wherein the flow channel (9) comprises a flow guide element (17), which conducts the breathing gas stream to the measurement portion (15) at a previously determined inflow angle of preferably greater than 10° and less than 170°.

15 Claims, 2 Drawing Sheets

(51) Int. Cl.
  *G01J 5/02*      (2006.01)
  *G01J 5/08*      (2006.01)
  *A61M 16/10*     (2006.01)

(52) U.S. Cl.
  CPC ............ *G01J 5/025* (2013.01); *G01J 5/0806* (2013.01); *G01J 5/0893* (2013.01); *A61M 2205/3306* (2013.01); *A61M 2205/3313* (2013.01); *A61M 2205/3368* (2013.01)

(58) Field of Classification Search
  CPC ............ A61M 16/1075; A61M 16/109; G01J 5/0014; G01J 5/02; G01J 5/025; G01J 5/0893; G01J 5/0806; G01J 5/0215; G01J 5/0225; G01J 5/0285; G01J 5/041; G01N 25/4826; G01K 2013/024; G01K 13/028
  USPC ............ 128/203.14, 204.22, 204.23
  See application file for complete search history.

(56) References Cited

U.S. PATENT DOCUMENTS

| | | | |
|---|---|---|---|
| 2003/0058919 A1* | 3/2003 | Ice | G01K 13/02 |
| | | | 374/138 |
| 2008/0105453 A1 | 6/2008 | Sparks et al. | |
| 2008/0225925 A1 | 9/2008 | Laverdiere et al. | |
| 2008/0283062 A1 | 11/2008 | Esposito, Jr. | |
| 2009/0041080 A1* | 2/2009 | Koch | A61M 16/16 |
| | | | 374/141 |

\* cited by examiner

TEMPERATURE MEASURING DEVICE FOR A RESPIRATORY HUMIDIFIER

FIELD OF INVENTION

The present invention pertains to a temperature-measuring device for a respiratory humidifier for ventilating patients with breathing gas.

BACKGROUND OF THE INVENTION

When patients are being mechanically ventilated on an intensive-care ward, for example, the patient to be ventilated is connected pneumatically to the respirator by a system of ventilation tubing. Because the breathing gas supplied to the patient must be adjusted with respect to temperature and humidity to meet the physiological needs of the patient, a respiratory humidifier is arranged in the inhalation or inspiration tube to heat and humidify the breathing gas. The respiratory humidifier usually comprises a liquid container filled with distilled water, the bottom plate of the container being in thermal contact with a heating plate in the housing, as a result of which the liquid is warmed. The inhalation gas is conducted into the liquid container, is thus humidified, and then leaves the liquid container at a certain temperature.

On the one hand, the temperature of the breathing gas is usually measured by the use of a temperature sensor arranged near the patient, the sensor being connected by an electrical measurement line to a control unit, which is arranged in the respiratory humidifier, for example. On the other hand, the temperature of the breathing gas is measured inside the respiratory humidifier, preferably as it enters and as it leaves the liquid container. The measured values are sent to a control unit present in the respiratory humidifier, which regulates the heating output of the humidifier.

Pyrometers or radiation thermometers for contactless temperature measurement are known in the art. These operate on the basis of the fact that every body with a temperature above 0 K emits thermal radiation; the intensity and position of the point of maximum emission depend on the temperature of the body. This radiation is detected and evaluated by the pyrometer. For temperature measurements around room temperature (from about 10° C. to about 40° C.), wavelengths in the mid-infrared region (MIR) will be used.

DE 10 2007 037 955 A1 discloses a contactless temperature-measuring device for a respiratory humidifier with a flow channel; in this device, a closed, hollow body for recording the temperature projects into the flow channel, and an infrared detector is directed toward the inside surface of the hollow body projecting into the flow channel. The disadvantage of this design of a temperature-measuring device is that it is not easy to manufacture a flow channel with a hollow body projecting into it, because either the hollow body must be formed out of the same material as the flow channel or perhaps bonded to it in a second production step, or alternatively the flow channel and the hollow body must be produced by means of separate molds, which is complicated and expensive. In addition, the hollow body in the flow channel is responsible for a relatively high flow resistance, which interferes with the flow of the breathing gas stream and thus reduces the flow rate.

It is therefore the object of the present invention to provide a temperature-measuring device for a respiratory humidifier which can be produced easily and at low cost and which nevertheless makes reliable contactless temperature measurement possible.

This object is achieved by the features of claim 1. Advantageous elaborations and embodiments are described in the subclaims.

SUMMARY OF THE INVENTION

According to one aspect of the invention, a temperature-measuring device is provided for a respiratory humidifier comprising a liquid container, wherein the temperature-measuring device comprises a flow channel for breathing gas and an infrared detector, which is directed from the outside toward the flow channel for the contactless detection of the temperature of the breathing gas in the flow channel, wherein the flow channel comprises, on its lateral surface, a measurement portion, which is aligned with the surrounding lateral surface areas and at which the infrared detector is directed, wherein the flow channel comprises a flow guide element, which conducts the breathing gas stream at a previously determined inflow angle of preferably greater than 10° and less than 170° to the measurement portion. The arrangement of the measurement portion on the lateral surface of the flow channel represents a simple design, because the measurement portion does not project from the lateral surface as it does in the case of DE 10 2007 037 955 A1, for example. The "lateral surface" as understood here is, for example, the wall surface of a cylindrical flow channel or a flat wall of a channel with a rectangular or polygonal cross section. Such flow channels can be designed as integral parts of the liquid container and can be easily produced at low cost either individually or together with the liquid container. The measurement portion is aligned two-dimensionally and more-or-less continuously with the surrounding areas of the lateral surface and/or is flush with those surfaces.

The inflow angle is preferably in the range from about 30° to about 60° and even more preferably in the range from about 40° to about 50°. A breathing gas stream striking the flow guide element set at this inflow angle is deflected directly onto the measurement portion, and as a result of its impact on the measurement portion, the breathing gas stream transfers a portion of its heat especially effectively to the material of the measurement portion. The temperature of the measurement portion thus corresponds even more accurately to what is essentially the temperature of the incident breathing gas stream.

It is especially advantageous for the flow guide element to be arranged in the interior of the flow channel. The flow guide element can be preferably a straight or a curved plate. With a flow guide element of this design, a breathing gas stream arriving in the longitudinal direction of the flow channel, for example, can be deflected at the preferred inflow angle. A flow guide element of this type in the interior of the flow channel is relatively easy to manufacture.

It is also possible, however, for the flow guide element to be a straight or curved tube with a rectangular, circular, polygonal, or elliptical cross section.

Alternatively, the flow channel itself can be designed to comprise a flow guide element. For this purpose, the flow channel itself can be bent in such a way or have a kink such that the desired inflow angle onto the measurement portion is obtained.

It is also advantageous for the surface of the flow guide element to have a structure. One possible structure is, for example, a set of holes; alternatively, the plate might be roughened or comprise a plurality of elevations or depressions, which can be of different shape, and so on. The structured surface serves to increase the turbulence of the breathing gas stream, so that it brings about the most homogeneous possible heating of the measurement portion. In addition, the turbulence of the breathing gas stream can also be helpful in increasing the uptake of moisture and heat by the breathing gas stream.

It is also advantageous for the measurement portion to be designed with thin walls and for the material of the measurements section to comprise an emissivity in the range from about 0.90 to about 1.00. Because the measurement wall is thinner than the walls of the adjacent lateral surface areas, the measurement portion heats up more quickly, and its temperature is also distributed more effectively, i.e., more homogeneously. In order to make the measurement especially accurate, the material should be thermally optimized, i.e., it should comprise an emissivity of close to 1.00. For this purpose, the measurement portion can be designed with a black coating layer, which is, for example, bonded in place or applied in some other way.

The infrared detector preferably comprises thermal infrared measuring elements such as bolometers, pyroelectric sensors, or thermopiles. Such infrared measuring elements are highly suitable for a temperature range in which respiratory humidifiers are preferably used, that is, in an ambient temperature range from about 10° C. to about 40° C. The person skilled in the art, however, can also use other types of infrared measuring elements suitable for the temperature range indicated above.

The infrared detector preferably comprises an optical component such as a lens so that it can be focused. It is also advantageous for the material of the flow channel or of the liquid container to comprise a transparent plastic such as LD-PE (Low Density Polyethylene). Transparency is advantageous, because the user can see from the outside whether or not any condensation has formed in the liquid container. Other suitable transparent plastic materials can also be used.

Also according to another aspect of the invention is a respiratory humidifier for a ventilator with a housing, a liquid container, and a temperature-measuring device as defined above, wherein the liquid container comprises a flow channel with a measurement portion, and the infrared detector is arranged on the housing.

A respiratory humidifier of this type advantageously comprises a first temperature-measuring device and a second temperature-measuring device, wherein the liquid container comprises a first flow channel for the introduction of breathing gas with a first measurement portion and a second flow channel for the discharge of breathing gas with a second measurement portion, and wherein the housing comprises a first and a second infrared detector, which are directed toward the first and second measurement portions for the temperature measurement.

It is advantageous for the respiratory humidifier to comprise a control unit, which is set up to regulate the heating output on the basis of the measurement value provided by the temperature-measuring device. It is obvious that, if there are two temperature measurement devices, the second will be used to measure the breathing gas stream being conducted away toward the top; this is therefore the stream which arrives from below, that is, which arrives in the liquid container from the surface of the liquid, and which is conducted onto the second measurement portion before it exits through the inhalation tube and proceeds to the patient through a tube-connecting element.

BRIEF DESCRIPTION OF THE DRAWINGS

The invention is explained in the following on the basis of a preferred exemplary embodiment with reference to the attached figures.

DETAILED DESCRIPTION

Figure 1:
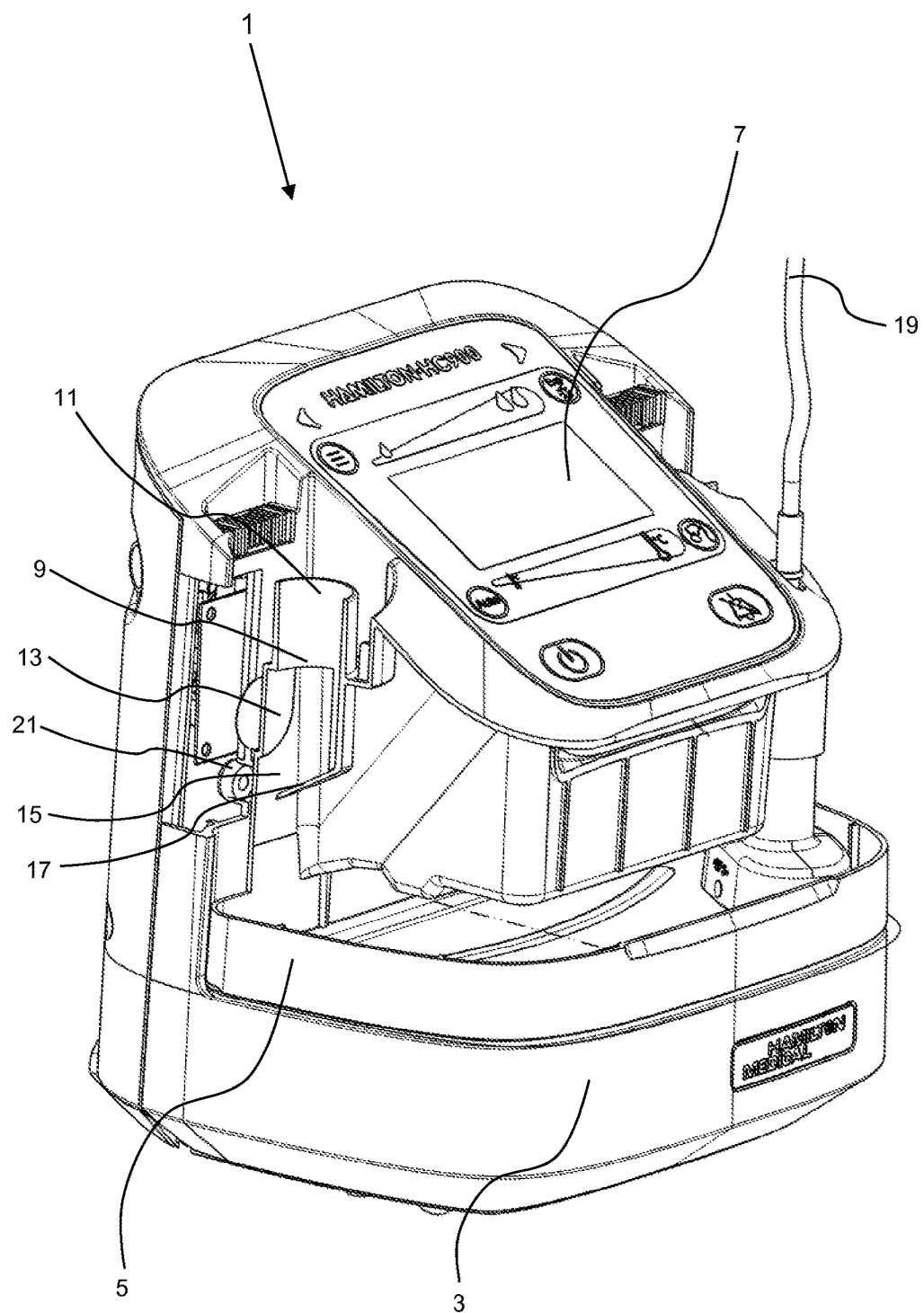
FIG. 1 shows a perspective and partially cut-away view of a respiratory humidifier comprising a preferred embodiment of the temperature-measuring device according to the invention.

FIG. 1 shows a perspective view of a respiratory humidifier 1 with a housing 3 and a liquid container 5, inserted detachably into the housing 3, wherein parts of the housing 3 and of the liquid container 5 have been cut away to facilitate a better understanding of the invention. The liquid container 5 has an essentially U-shaped cross section in the horizontal direction, so that, after it has been inserted laterally/horizontally into the housing 3, it surrounds the central projecting section of the housing 3, on the top surface of which the user interface 7 with display and operating elements is arranged. In the area of the liquid container 5 shown on the left in FIG. 1, the container comprises a flow channel 9, which begins at a tubular socket 11 with a circular cross section and extends downward therefrom in the form of a lateral surface 13. The lateral surface 13, which is defined as the two-dimensional wall surface surrounding the flow channel 9, comprises a measurement portion 15, the wall of which is thinner than that of the rest of the lateral surface 13. The measurement portion 15 is aligned with the surrounding area of the lateral surface 13 or is flush with them, not having any element projecting or protruding from the lateral surface 13 into the interior of the flow channel 9. In the embodiment illustrated here, the flow channel 9 comprises a flow guide element 17, which extends over approximately three-fourths of the cross section of the flow channel 9 as an essentially flat plate from the lateral surface section opposite the lateral surface 13 at an angle of approximately 60° to the measurement portion 15.

The liquid container 5 shown here is made of transparent plastic material, so that the liquid in it and any accumulations of condensate can be seen from the outside. The liquid container 5 also comprises an upward-extending refill tube 19, through which fresh liquid can be added automatically to the liquid container 5 from an external reservoir. In the area on the left, the housing 3 comprises a wall (partially cut away in FIG. 1), which, when the humidifier is in operation, is parallel to the lateral surface 13 of the liquid container 5, wherein only a narrow air gap is present between the two surfaces. In this wall of the housing, an infrared detector 21 is arranged in a recess, the lens of which is directed toward the measurement portion 15 of the lateral surface 13.

Figure 2:
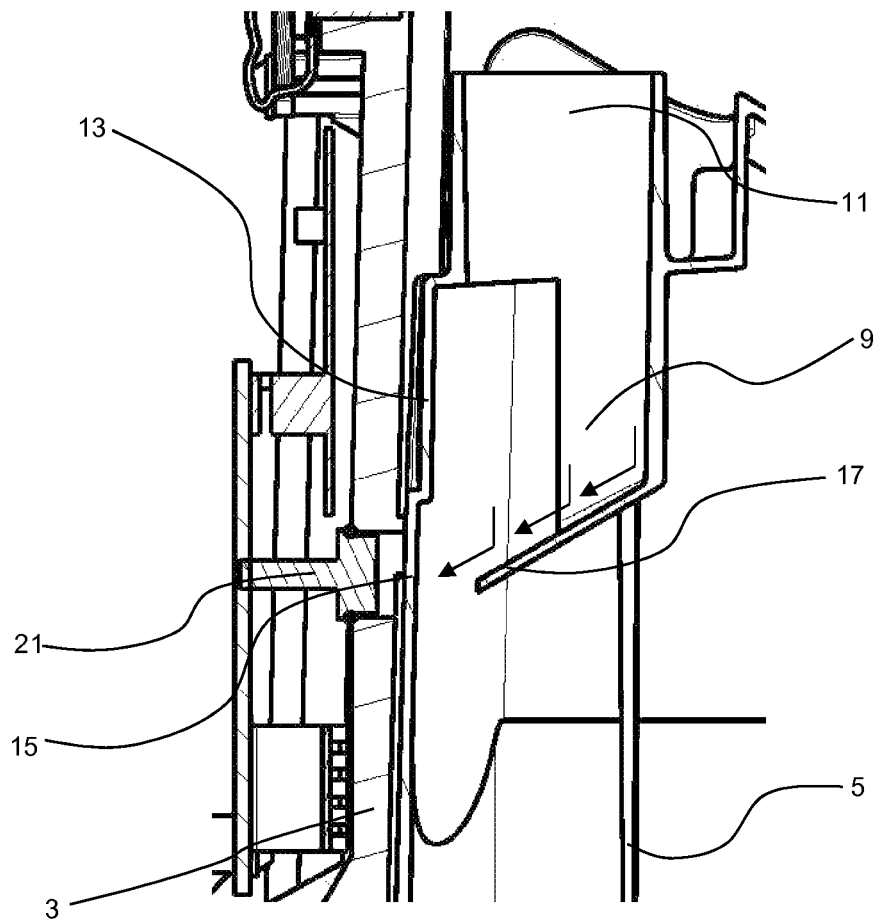
FIG. 2 shows a side view of the essential elements of the preferred embodiment of the present invention illustrated in FIG. 1.

FIG. 2 shows a lateral cross-sectional view of the preferred embodiment of FIG. 1 of the temperature-measuring device according to the invention. The cross-sectional view of the part shown is enlarged and omits the remaining elements of the respiratory humidifier, which are not essential to the present invention. It can be clearly seen how the flow guide element 17 deflects the breathing gas stream in the flow channel 9 entering through the tubular socket 11 onto the measurement portion 15. The three arrows indicate in principle the flow direction of the breathing gas stream at the flow guide element 17.

In the left part of FIG. 2, it is easy to recognize the shaded infrared detector 21, which is oriented horizontally at the measurement portion 15 from outside the liquid container 5. The infrared detector 21 is connected to a control unit (not shown), which is installed on the housing 3 to evaluate the measurement signal and to regulate the temperature or heating output accordingly.

The preferred embodiment described above represents a simple solution for the contactless temperature measurement of the breathing gas stream in the liquid container 5 of the respiratory humidifier 1, because the measurement portion 15 is easily formed in the lateral surface 13 of the flow channel 9, and the flow guide element 17 can also be formed easily inside the flow channel 9. It is also conceivable that the flow guide element 17 could be of multi-part design, curved, or structured, or it could be provided with a different inflow angle with respect to the measurement portion 15 as a way of optimizing the incoming flow and thus the temperature distribution on the measurement portion 15.

With the subject matter of the present invention, a temperature-measuring device for a respiratory humidifier has been provided, which can be produced easily and at low cost and which nevertheless makes it possible to obtain a reliable, contactless temperature measurement.

The invention claimed is:

1. In a temperature-measuring device for a respiratory humidifier with a liquid container, the temperature-measuring device including a flow channel for breathing gas and an infrared detector directed from the outside toward a measurement portion in the flow channel for contactless detection of the temperature of the breathing gas in the flow channel, the improvement comprising:
   a wall surface surrounding and defining the flow channel and having the measurement portion as a section thereof, the measurement portion being flush with surrounding areas of the wall surface without the measurement portion projecting or protruding into the interior of the flow channel; and
   a flow guide element within the flow channel, the flow guide element being separate from the wall surface and positioned and configured to deflect the breathing gas stream directly toward the measurement portion at an inflow angle of greater than 10° and less than 170° with respect to the measurement portion.

2. The temperature-measuring device of claim 1 wherein the inflow angle is greater than 30° and less than 60°.

3. The temperature-measuring device of claim 2 wherein the inflow angle is greater than 40° and less than 50°.

4. The temperature-measuring device of claim 1 wherein the flow guide element is arranged in the interior of the flow channel.

5. The temperature-measuring device of claim 4 wherein the flow guide element is a straight or curved plate.

6. The temperature-measuring device of claim 1 wherein the flow guide element is a straight or curved tube with a rectangular, circular, polygonal, or elliptical cross-section.

7. The temperature-measuring device of claim 6 wherein the flow guide element comprises a structured surface.

8. The temperature-measuring device of claim 1 wherein the flow guide element comprises a structured surface.

9. The temperature-measuring device of claim 1 wherein the measurement portion is formed with thin walls having an emissivity in the range between 0.90 and 1.00.

10. The temperature-measuring device according claim 1 wherein the infrared detector comprises thermal infrared measuring elements such as bolometers, pyroelectric sensors, or thermopiles.

11. The temperature-measuring device of claim 1 wherein the infrared detector comprises an optical component for focusing.

12. The temperature-measuring device of claim 1 wherein the material of the flow channel is a transparent plastic.

13. In a respiratory humidifier for a ventilator including a housing, a liquid container, and a temperature-measuring device having a flow channel for breathing gas and an infrared detector directed from the outside toward a measurement portion in the flow channel for contactless detection of the temperature of the breathing gas in the flow channel, the improvement comprising:
   a wall surface surrounding and defining the flow channel and having the measurement portion as a section thereof, the measurement portion being flush with surrounding areas of the wall surface without the measurement portion projecting or protruding into the interior of the flow channel; and
   a flow guide element within the flow channel, the flow guide element being separate from the wall surface and positioned and configured to deflect the breathing gas stream directly toward the measurement portion at an inflow angle of greater than 10° and less than 170° with respect to the measurement portion.

14. The respiratory humidifier of claim 13 wherein the liquid container includes the flow channel with the measurement portion and the infrared detector is arranged on the housing.

15. The respiratory humidifier of claim 13 including a control unit to regulate the heating output based on the measurement value provided by the temperature-measuring device.

* * * * *